United States Patent
Zubizarreta (10) Patent No.: US 7,644,091 B1
(45) Date of Patent: Jan. 5, 2010

(54) COMPUTER-IMPLEMENTED MEDICAL INFORMATION INDEXING SYSTEM AND METHOD

(75) Inventor: Miguel A. Zubizarreta, Westlake, OH (US)

(73) Assignee: Hyland Software, Inc., Westlake, OH (US)

( * ) Notice: Subject to any disclaimer, the term of this patent is extended or adjusted under 35 U.S.C. 154(b) by 203 days.

(21) Appl. No.: 11/084,710

(22) Filed: Mar. 18, 2005

Related U.S. Application Data (60) Provisional application No. 60/554,168, filed on Mar. 18, 2004.

(51) Int. Cl.
*G06F 17/30* (2006.01)
*G06F 7/00* (2006.01)

(52) U.S. Cl. .................. 707/101; 707/104.1; 707/102

(58) Field of Classification Search .................. 707/101, 707/104.1
See application file for complete search history.

(56) References Cited

U.S. PATENT DOCUMENTS

| 5,471,615 | A | 11/1995 | Amatsu et al. |
| 5,664,109 | A * | 9/1997 | Johnson et al. ................. 705/2 |
| 5,912,818 | A * | 6/1999 | McGrady et al. ............ 700/232 |
| 5,942,986 | A * | 8/1999 | Shabot et al. ............... 340/7.29 |
| 6,912,522 | B2 | 6/2005 | Edgar |
| 6,999,972 | B2 | 2/2006 | Lusen et al. |
| 7,308,646 | B1 | 12/2007 | Cohen et al. |
| 2002/0128870 | A1* | 9/2002 | Whitson ........................ 705/3 |
| 2002/0184325 | A1 | 12/2002 | Killcommons et al. |
| 2002/0194026 | A1* | 12/2002 | Klein et al. ..................... 705/2 |
| 2003/0126156 | A1* | 7/2003 | Stoltenberg et al. ....... 707/104.1 |
| 2004/0006433 | A1* | 1/2004 | Robson et al. ................ 702/20 |

OTHER PUBLICATIONS

Verity Incorporated, Vertity Collection Reference Guide for People Soft, Verity Inc., Version 5.0.1., p. 47, http://download-west.oracle.com/docs/cd/B28726_01/psft/acrobat/pt846vvc-b0205.pdf, Nov. 15, 2003.*

* cited by examiner

*Primary Examiner*—Kuen S Lu
(74) *Attorney, Agent, or Firm*—Jones Day

(57) ABSTRACT

Systems and methods to receive HL7 electronic medical data and to create an electronic indexing medical record based upon the received HL7 electronic medical data. The indexing medical record is provided to a document management system, wherein the document management system is configured to use the provided indexing medical record to index a medically-related document.

17 Claims, 7 Drawing Sheets

COMPUTER-IMPLEMENTED MEDICAL INFORMATION INDEXING SYSTEM AND METHOD

CROSS-REFERENCE TO RELATED APPLICATION

This application claims priority to and the benefit of U.S. Provisional Application Ser. No. 60/554,168, filed on Mar. 18, 2004, of which the entire disclosure (including any and all figures) is incorporated herein by reference.

TECHNICAL FIELD AND BACKGROUND

This relates generally to handling medical information and more particularly to computer-implemented methods and systems to handle HL7 electronic medical records.

Health Level Seven (HL7) is an American National Standards Institute (ANSI) standard for the cross-platform exchange of information for health care organizations. HL7 is directed to specifying the seventh level of the ISO communications model which is the application layer. Accordingly, HL7 deals with the formatting or structure of the information, not the technical details of how the information is passed from one system to another. This allows HL7 to be independent of technologies and platforms and to be implemented using a variety of software technologies.

SUMMARY

In accordance with the teachings provided herein, systems and methods for operation upon data processing devices are provided in order to overcome one or more of the aforementioned disadvantages or other disadvantages. For example, a system and method can be configured to receive HL7 electronic medical data and create an electronic indexing medical record based upon the received HL7 electronic medical data. The indexing medical record is provided to a document management system, wherein the document management system is configured to use the provided indexing medical record to index a medically-related document.

DETAILED DESCRIPTION

Figure 1:
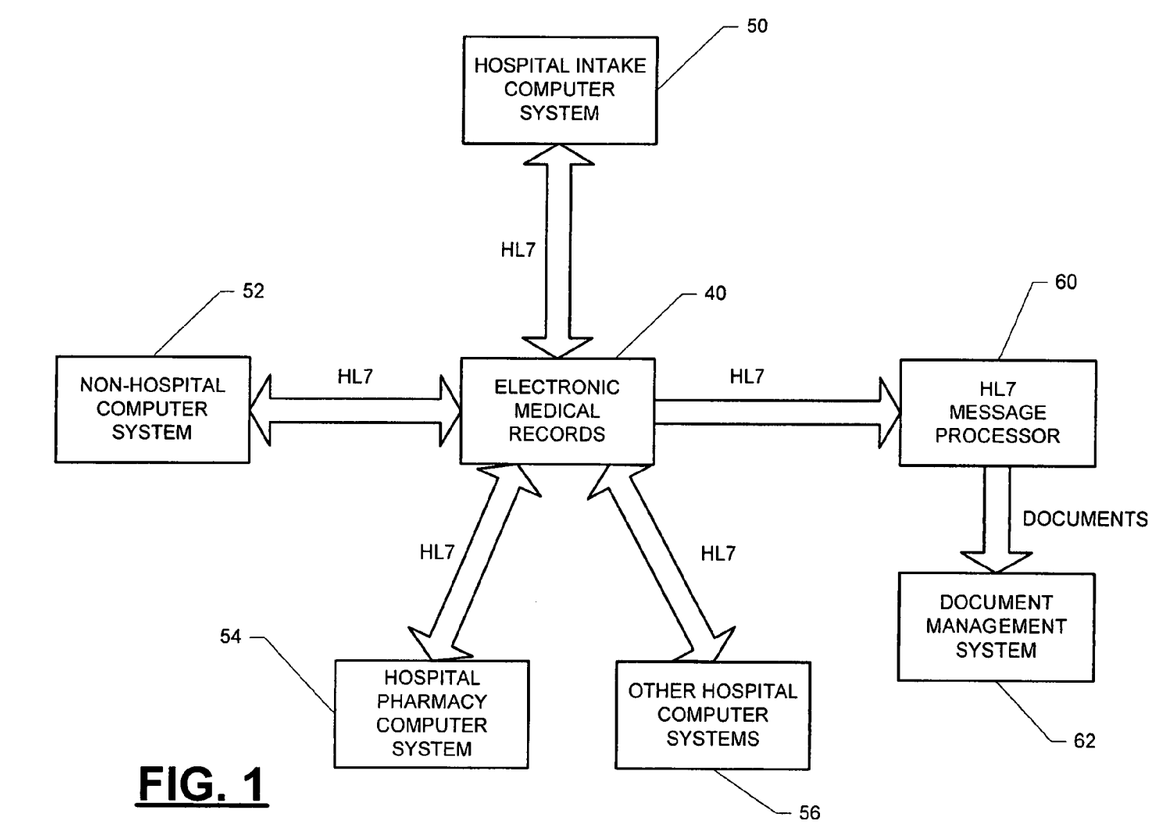
FIG. 1 is a block diagram depicting the HL7 messaging protocol that allows different health information systems to communicate among themselves.

As shown in FIG. 1, the HL7 common messaging protocol allows different health information systems (50, 52, 54, 56) to communicate among themselves even though the systems may have been developed independently from each other. As an example of HL7 message passing, when a patient is admitted to a hospital, a hospital's intake computer system captures details about the patient, such as patient demographic information as well as admission information (e.g., admitting doctor, ward, financial details, etc.). Other hospital information systems such as a hospital pharmacy system could utilize this information. To accomplish this, a message 40 formatted according to the HL7 standard is sent from the intake system to each of the interested systems in the hospital about the patient. The HL7 message may be sent automatically to the other systems or may be sent upon request of the other systems. Because the message is formatted according to the HL7 standard, the message can be parsed and understood by the other systems.

An HL7 message processor 60 is provided to expand the use of HL7 messages. This includes creating documents from the HL7 messages for storage, retrieval and other utilization within a document management system 62.

Figure 2:
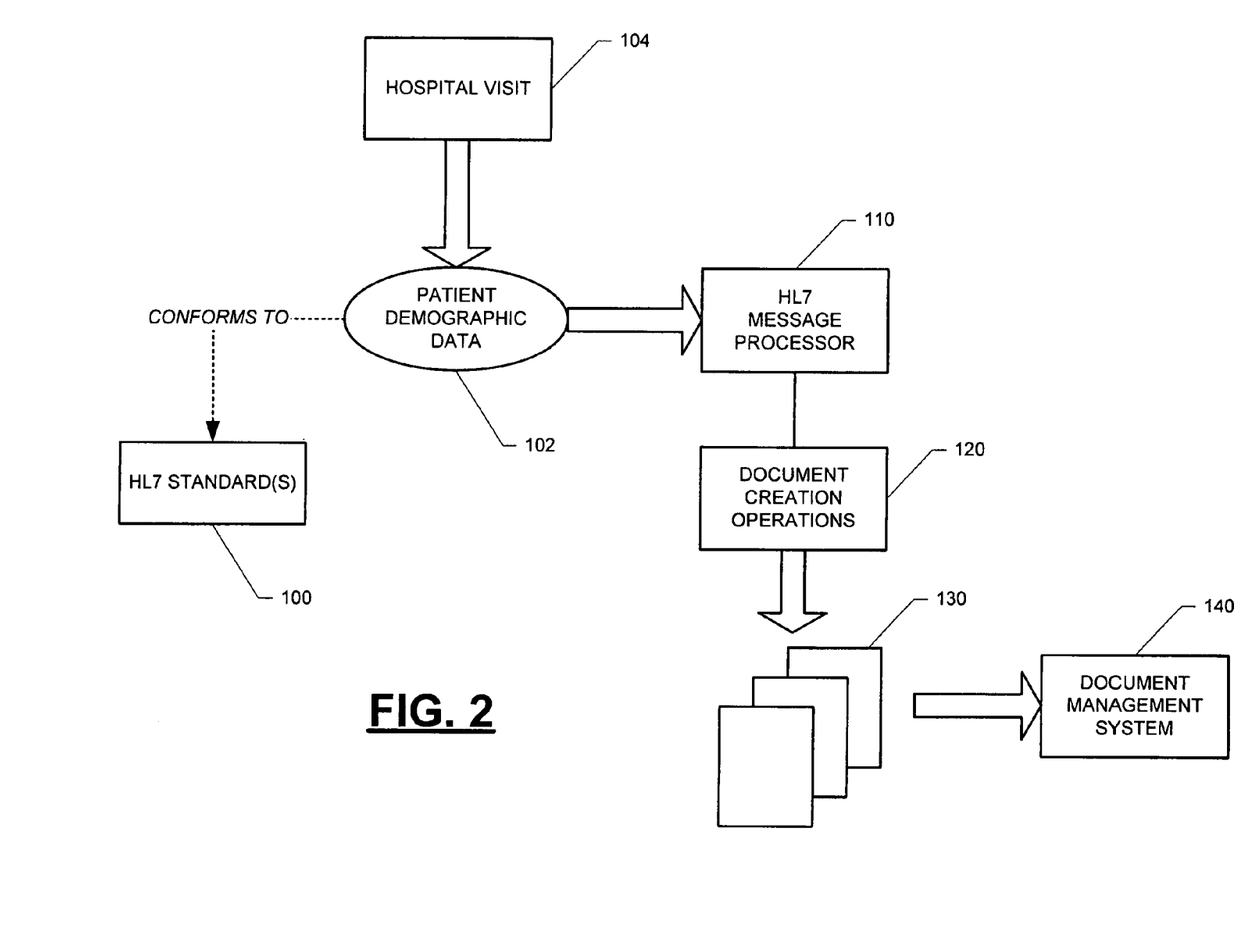
FIG. 2 is a block diagram depicting one or more documents being created from an HL7 patient demographic message for storage in a document management system.

FIG. 2 illustrates one or more documents 130 being created from an HL7 patient demographic message 102 for storage in a document management system 140. First, a person entering the hospital as a patient will have their demographic information obtained. An HL7 patient demographic message 102 is generated that contains data segments for storing patient demographic information. Each segment has a three character name and a pre-defined format of specific fields. The segments group related information together. For example, a segment may contain patient name, address and date of birth.

An HL7 message processor 110 analyzes the information contained in the segments of the HL7 demographic message 102 and creates via operations 120 a document 130 for storage in the document management system. The document may be any type (e.g., a text document, PDF document, word processing document, spreadsheet document, etc.) and can be created based upon a template that defines the fields to include in the created document as well as the order and format of the fields in the document.

If desired, the document management system 140 may create an electronic form that is pre-populated with the data parsed by the HL7 message processor 110. The pre-populated form can then be routed through a document management work flow that allows for completion of the form by different workstations.

Figure 3:
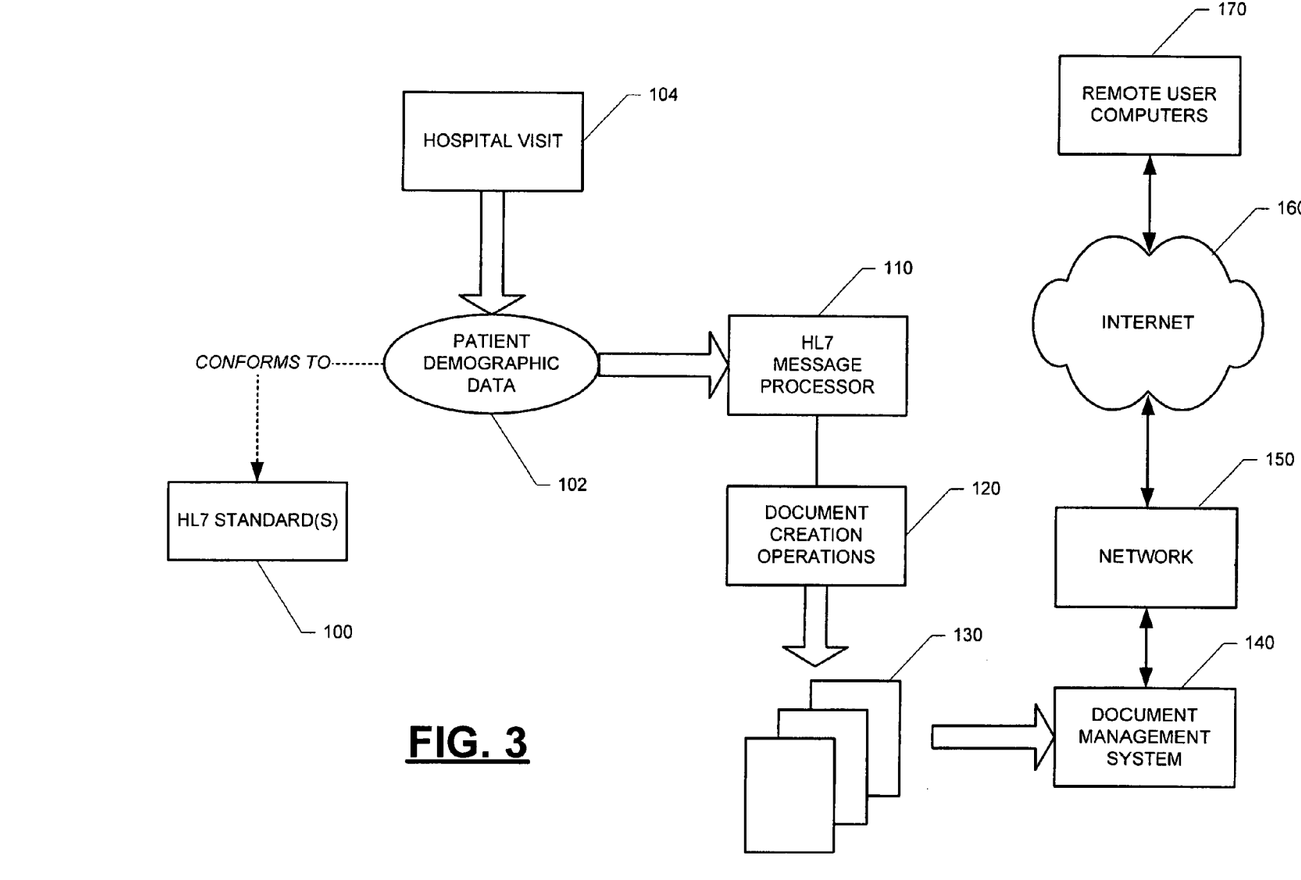
FIG. 3 is a block diagram depicting a document being generated from an HL7 message that can be made available over a network to remote users.

As another example of the wide number of uses for an HL7 message processor 110, FIG. 3 depicts a document 130 being generated from an HL7 message 102 that can be made available over a network 150 to remote users 170. In such a configuration, doctors, while away from the hospital, can utilize the searching features of the document management system 140 to locate their patients' documents in the document management system 140 that were created by the HL7 message processor 110.

Many different types of data management systems may be used with an HL7 message processor, such as the OnBase software system from Hyland Software, Inc. (located in Westlake, Ohio). The OnBase system electronically captures, stores and manages documents generated or received by a company. The software handles everything a user needs to do with those documents, such as retrieve documents based upon keywords and indexes, revise, annotate, distribute, or post to a website. It integrates seamlessly with ERP, CRM, and other applications to create a single point of online access to all relevant document information.

Figure 4:
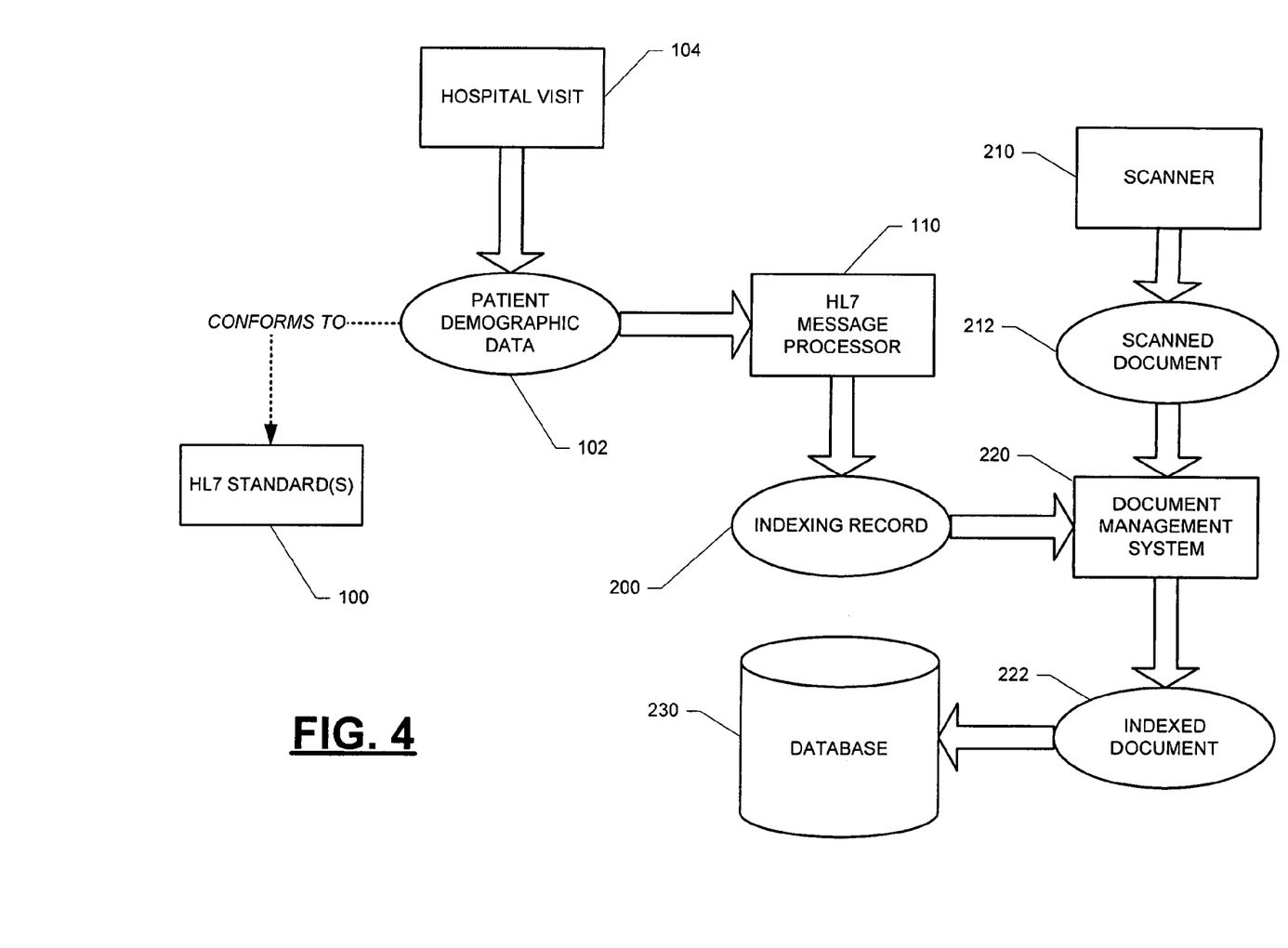
FIG. 4 is a block diagram depicting an HL7 message processor generating an indexing record from an HL7 message for use in indexing of medical records.

FIG. 4 shows other capabilities of an HL7 message processor 110. In FIG. 4, an HL7 message processor 110 generates an indexing record 200 from an HL7 message 102 for use in indexing of medical records 222 in a database 230. With the created indexing record 200, any document, such as those documents 212 generated by a document scanner 210, that might occur at a later point in time could use that indexing record 200.

Figure 5:
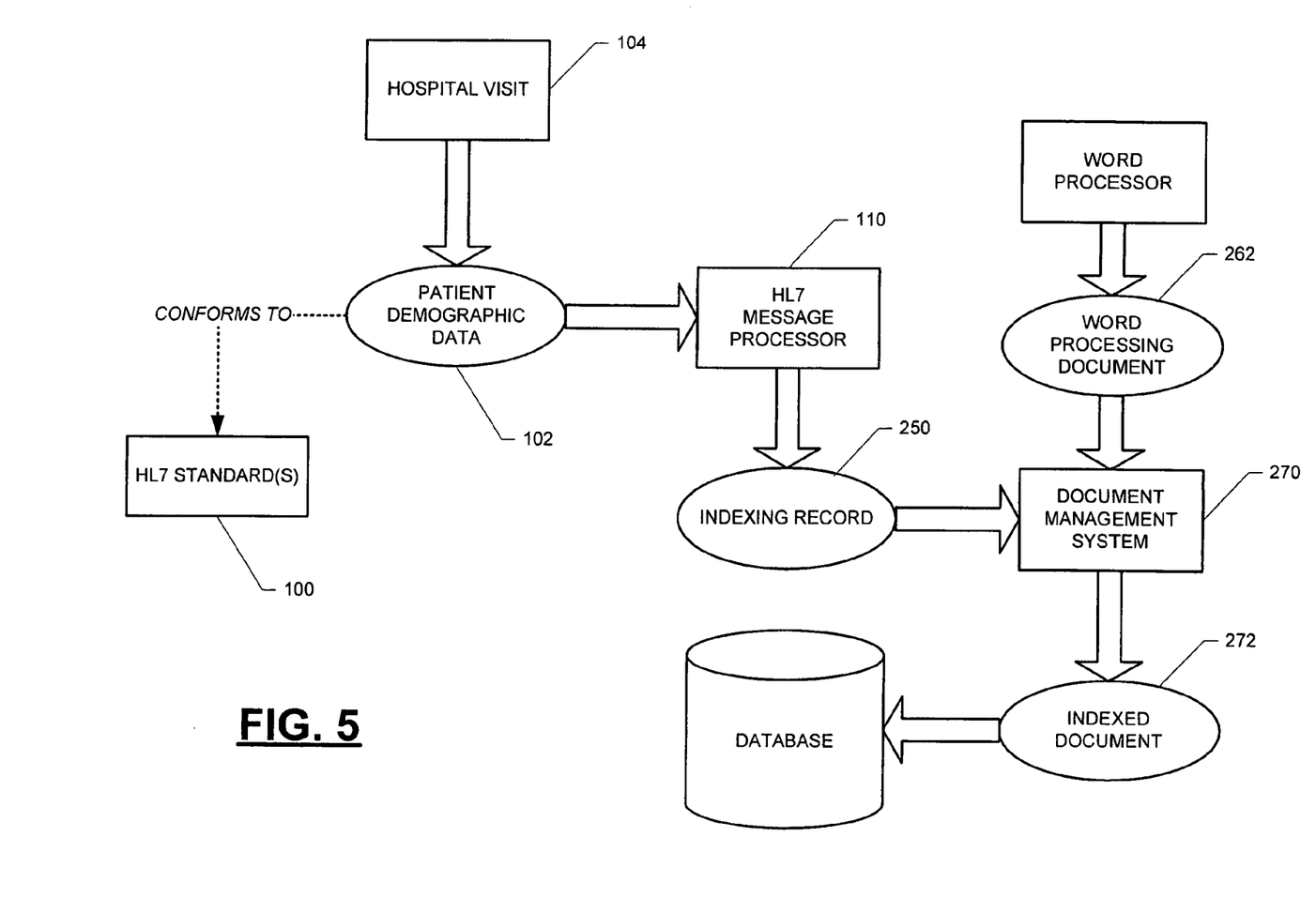
FIG. 5 is a block diagram depicting other document management system operations using the indexing record that is created from one or more HL7 messages.

FIG. 5 illustrates that many other document management system operations may use the indexing record 250 that is created from one or more HL7 messages. As an example, a user entering a word processing document 262 into a document management system 270 can select from a list of patients that this document is for a particular patient. Selection of a name from the list would result in the document 272 being automatically indexed in the document management system 270 through use of the created indexing record 250. In this way, documents are indexed into a document management system by using one or more HL7 records to create indexing records. The created indexing records may also automatically pre-populate fields in a document.

Figure 6:
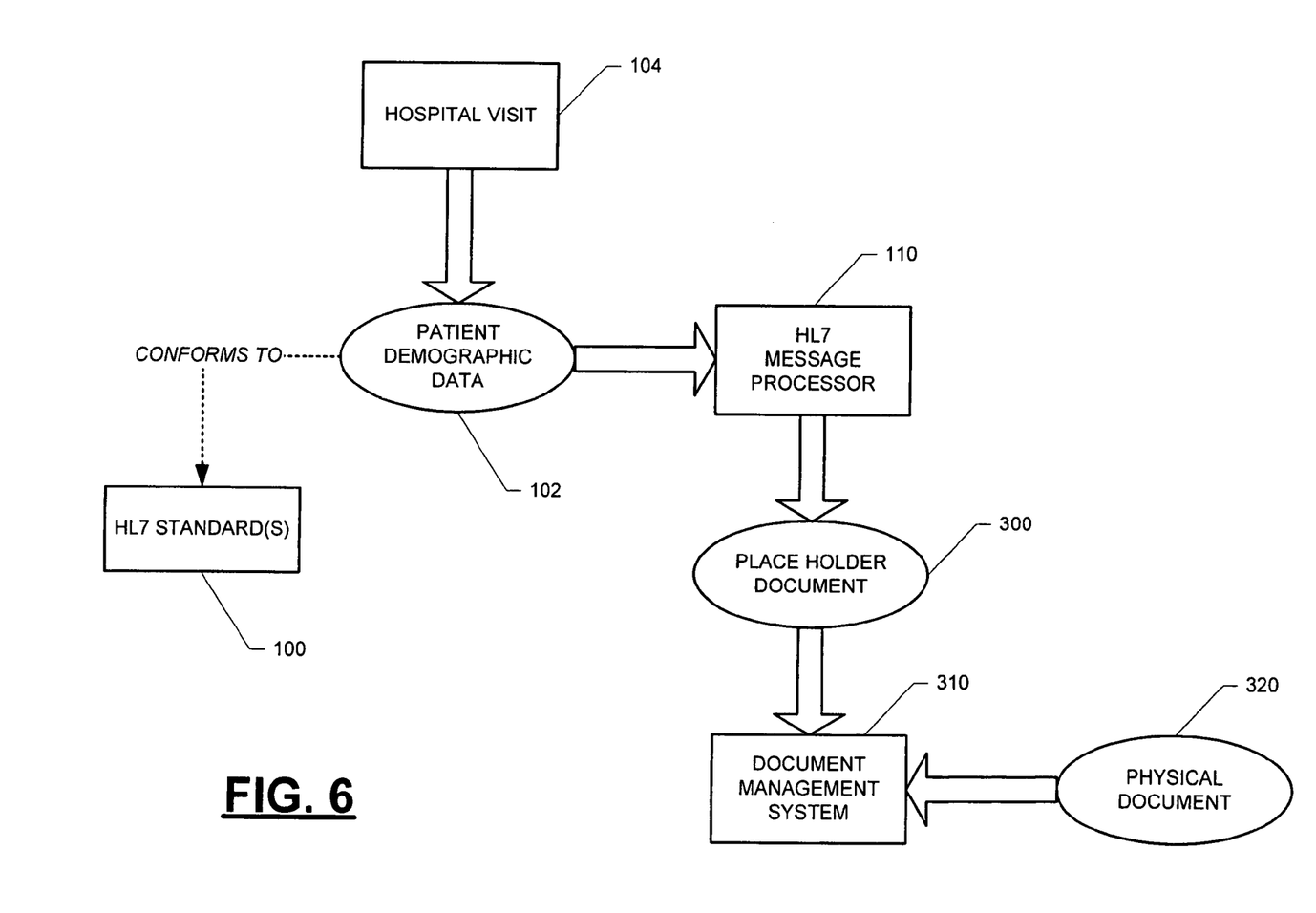
FIG. 6 is a block diagram depicting an HL7 message processor using one or more HL7 messages to create a place holder document whose expected physical file is to be attached at some later point in time.

FIG. 6 illustrates that an HL7 message processor 110 may be configured to use one or more HL7 messages 102 to create in the document management system 310 a place holder document 300 whose expected physical file 320 is to be attached at some later point in time. This helps verify that physical documents are eventually created that correspond to the place holder document. As part of the document verification process, a report can be generated that lists which documents have not arrived within a predetermined amount of time of a place holder document being created. In this way, documents that are missing or delayed by more than a certain period of time can be identified.

While examples have been used to disclose the invention, including the best mode, and also to enable any person skilled in the art to make and use the invention, the patentable scope of the invention is defined by claims, and may include other examples that occur to those skilled in the art. As an example of the wide range and scope of the systems and methods disclosed herein, many different types of organizations may use the systems and methods disclosed herein, such as hospitals and other users of HL7 electronic medical data. Organizations may use the capabilities of an HL7 message processor disclosed herein either separately or together.

As another example, data signals that are transmitted using a communication channel (e.g., a network) may be used with the systems and methods disclosed herein. The data signals can include any type of HL7 message data or document created therefrom and depending upon the implementation environment may be packetized data that is transmitted through a carrier wave or other medium across the network. Still further computer-readable media may be provided to and used with a computer system that is capable of causing a computer to perform the methods and implement the systems disclosed herein.

Figure 7:
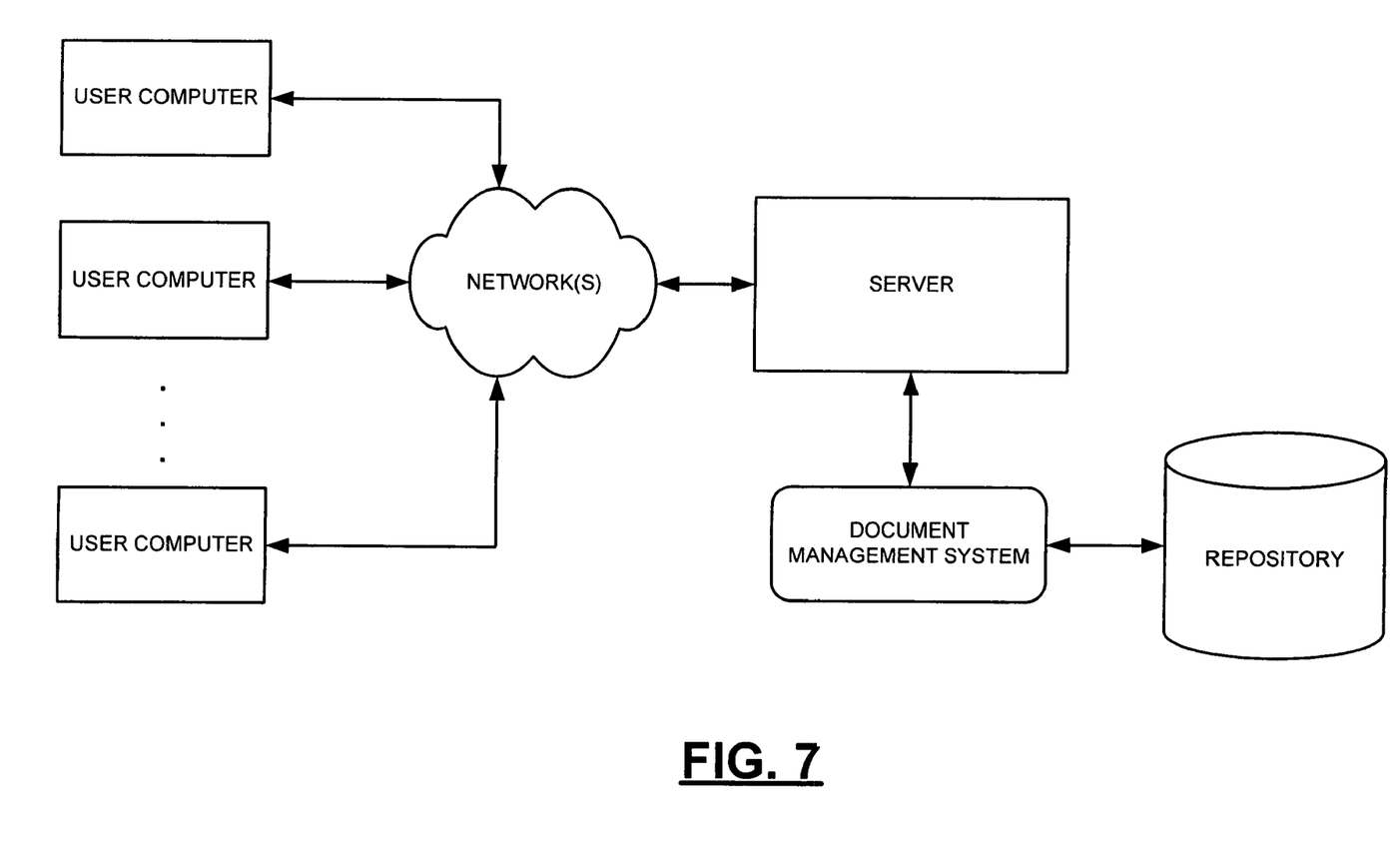
FIG. 7 is a block diagram depicting a network having access to a document management system.

It is further noted that the systems and methods may be implemented on various types of computer architectures, such as for example on a single general purpose computer or workstation or on a networked system (e.g., internet or intranet networks) as shown in FIG. 7.

The user computer's interface screens can receive web pages accessible over a network such as over the world-wide web (web). The web is a method of accessing information on the Internet which allows a user to navigate the Internet resources intuitively, without IP addresses or other technical knowledge. A user's computer can contain client software, known as a web "browser," which is used to display web pages as well as traditional non-web files on the client system.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The systems' and methods' data (e.g., associations, mappings, etc.) may be stored and implemented in one or more different types of computer-implemented ways, such as different types of storage devices and programming constructs (e.g., data stores, RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions and data structures described herein may be connected directly or indirectly to each other in order to allow the flow of data needed for their operations. It is also noted that software instructions or a module can be implemented for example as a subroutine unit of code, or as a software function unit of code, or as an object (as in an object-oriented paradigm), or as an applet, or in a computer script language, or as another type of computer code or firmware. The software components and/or functionality may be located on a single device or distributed across multiple devices depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context clearly dictates otherwise; the phrase "exclusive or" may be used to indicate situation where only the disjunctive meaning may apply.

It is claimed:

1. A computer-implemented method for handling Health Level Seven (HL7) electronic medical data, comprising the steps of:
    receiving HL7 electronic medical data;
        wherein the HL7 electronic medical data includes data segments,
        wherein a segment has a three character name and a pre-defined format of specific fields;
    creating an electronic indexing medical record based upon the received HL7 electronic medical data;
    creating a medically-related document containing data from the received HL7 electronic medical data;
    providing the indexing medical record and the medically-related document to a document management system;
        wherein the document management system is configured to store the medically-related document and to use the provided indexing medical record in order to index the medically-related document.

2. The method of claim 1, wherein HL7 is an American National Standards Institute (ANSI) standard for cross-platform exchange of information within a health care organization.

3. The method of claim 1, wherein HL7 is directed to level seven of the ISO (International Standards Organization) communications model.

4. The method of claim 1, wherein the HL7 electronic medical data includes hospital patient demographic data.

5. The method of claim 1, wherein a user interface provides data in order to retrieve the created medically-related document based upon the indexing medical record.

6. The method of claim 1, wherein the received HL7 electronic medical data is used to create in the document management system a place holder document whose expected physical file is to be subsequently attached.

7. The method of claim 1, wherein the created electronic indexing medical record is used to index documents within the document management system that are generated subsequent to the creating of the electronic indexing medical record.

8. The method of claim 1, wherein the HL7 electronic medical data includes admission information.

9. A computer-implemented system for handling Health Level Seven (HL7) electronic medical data, comprising:
   means for receiving HL7 electronic medical data;
      wherein the HL7 electronic medical data includes data segments,
      wherein a segment has a three character name and a pre-defined format of specific fields;
   an HL7 message processor configured to execute in a computer system and to create an electronic indexing medical record based upon the received HL7 electronic medical data;
   said HL7 message processor creating a medically-related document containing data from the received HL7 electronic medical data;
      wherein the indexing medical record and the medically-related document are provided to a document management system;
      wherein the document management system is configured to execute in the computer system and to store the medically-related document and to use the provided indexing medical record in order to index the medically-related document.

10. The system of claim 9, wherein HL7 is an American National Standards Institute (ANSI) standard for cross-platform exchange of information within a health care organization.

11. The system of claim 9, wherein HL7 is directed to level seven of the ISO (International Standards Organization) communications model.

12. The system of claim 9, wherein the HL7 electronic medical data includes hospital patient demographic data.

13. The system of claim 9, wherein a user interface provides data in order to retrieve the created medically-related document based upon the indexing medical record.

14. The system of claim 9, wherein the received HL7 electronic medical data is used to create in the document management system a place holder document whose expected physical file is to be subsequently attached.

15. The system of claim 9, wherein the created electronic indexing medical record is used to index documents within the document management system that are generated subsequent to the creating of the electronic indexing medical record.

16. The system of claim 9, wherein the HL7 electronic medical data includes admission information.

17. Computer-readable storage medium encoded with instructions that cause a computer to perform a method for handling Health Level Seven (HL7) electronic medical data, said method comprising the steps of:
   receiving HL7 electronic medical data;
   wherein the HL7 electronic medical data includes data segments, wherein a segment has a three character name and a pre-defined format of specific fields;
   creating an electronic indexing medical record based upon the received HL7 electronic medical data;
      creating a medically-related document containing data from the received HL7 electronic medical data;
      providing the indexing medical record and the medically-related document to a document management system;
   wherein the document management system is configured to store the medically-related document and to use the provided indexing medical record in order to index the medically-related document.

\* \* \* \* \*